United States Patent [19]

Nuss, Jr. et al.

[11] 4,187,317
[45] Feb. 5, 1980

[54] SUNSCREEN AND ERYTHEMA TREATING WITH N-BENZYLIDENE ANILENES

[75] Inventors: George W. Nuss, Jr., Lansdale; Norman J. Santora, Roslyn; George H. Douglas, Malvern, all of Pa.

[73] Assignee: William H. Rorer, Inc., Fort Washington, Pa.

[21] Appl. No.: 942,868

[22] Filed: Sep. 15, 1978

Related U.S. Application Data

[63] Continuation-in-part of Ser. No. 839,960, Oct. 6, 1977.

[51] Int. Cl.$^2$ .................. A61K 31/24; A61K 31/135; A61K 31/195
[52] U.S. Cl. .................................. 424/309; 424/319; 424/330
[58] Field of Search .................. 424/59, 330, 309, 319

[56] References Cited

U.S. PATENT DOCUMENTS

| 3,833,606 | 9/1974 | Mohan | 260/310 C |
|---|---|---|---|
| 3,862,833 | 1/1975 | Johnson | 71/121 |
| 3,947,587 | 3/1976 | Negrevergne | 424/285 |
| 3,993,645 | 11/1976 | Crouse et al. | 260/240 D |
| 4,047,803 | 9/1977 | Yaguchi | 350/160 |
| 4,122,026 | 10/1978 | Osman | 252/299 |

OTHER PUBLICATIONS

Kadaba et al., J. Heter. Chem., vol. 4, pp. 301–304 (1967).
Goetz, J. Heter. Chem., vol. 5, pp. 501–507 (1968).
Bellobono et al., Tetrahedron, vol. 25, pp. 57–71 (1969).
Pavini et al., Gazz. Chem. Ital., vol. 96, pp. 1423–1431 (1966).
Ogata et al., J. Chem. Soc., Perkin Trans., vol. 2, pp. 792–797 (1972).

Primary Examiner—Stanley J. Friedman
Attorney, Agent, or Firm—Miller & Prestia; James A. Nicholson

[57] ABSTRACT

Compositions for treating radiation induced erythemas and for protecting the human skin against the harmful effects of sunlight, containing as the active ingredient N-benzylideneaniline and its derivatives.

31 Claims, No Drawings

SUNSCREEN AND ERYTHEMA TREATING WITH N-BENZYLIDENE ANILENES

BACKGROUND OF THE INVENTION

This is a continuation-in-part of our co-pending application Ser. No. 839,960, filed Oct. 6, 1977.

This invention relates to new and useful radiation screening preparations and to methods of protecting the human skin against the harmful effects of sunlight.

The skin responds differently to the different wavelengths of electromagnetic radiation. In sunlight, visible and infrared radiation (3900 A. to 14,000 A.) produce a transient reddening of the skin. The well known tanning effect of the sun is a result of exposure to near ultraviolet radiation between 3200 A. and 3900 A. which is pigmetogenic. The ultraviolet radiation of between 2900 A. and 3200 A. will induce erythema which may be severe in fair-skinned individuals. It is the object of sunscreen agents to prevent erythema of the skin by ultraviolet rays having a wavelength between 2900 A. and 3200 A. Conventional sun-screen agents are classified according to how they accomplish this object.

One group of conventional sunscreen powders protects the skin by forming a reflective barrier thereon. Examples of such agents are kaolin, talc and pigments such as zinc oxide, magnesium carbonate, aluminum hydroxide and the like. Most common pigments also exhibit some absorption of ultraviolet light. The use of such powders and/or pigments has been rather limited because of the difficulty in applying them to the entire body and their unattractiveness when used over large areas.

A second major group of sunscreens or light screens protects the skin by absorption of wavelengths in the erythemal range, i.e. between about 2900 A. and 3900 A. The comparative effectiveness of such substances as aids in tanning is at least partially dependent on degree of adsorption of tanning wavelengths in addition to adsorption of wavelengths in the erythemal range. Many such agents are known, as will be further explained hereinafter.

It has been noted by Andrew P. Warin in *British Journal of Dermatology* (1978), Vol. 98, p. 474, "Ultra-Violet Erythemas in Man", that the formation of prostaglandins are a cause of the inflammatory action in humans resulting from the sun's erythema producing rays. Therefore, in order to prevent the sun from causing erythemas in man it is necessary to either block the sun's rays or to inhibit the formation of prostaglandins. It has been surprisingly found in accordance with the present invention that certain anti-inflammatory compounds possess the additional ability to not only protect the human skin against potentially harmful ultraviolet rays of sunlight or artificial light in the total spectrum but to inhibit the formation of prostaglandins. The combination of useful properties permits the compounds of the present invention to be applied not only to obtain relief from existing sun-produced erythemas but to further act as a sunscreen and prevent additional erythemas from occurring.

BRIEF DESCRIPTION OF THE INVENTION

The present invention pertains to sunscreening and erythema-treating preparations containing as an active ingredient a compound of the formula:

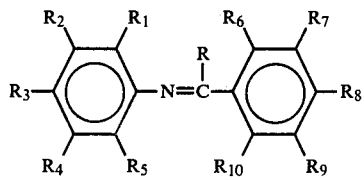

where:

R is hydrogen or alkyl;

$R_1$, $R_2$, $R_3$, $R_4$, $R_5$, $R_6$, $R_7$, $R_8$, $R_9$, and $R_{10}$ may be the same or different and are hydrogen, alkyl, cyano, nitro, amino, haloloweralkoxy, haloloweralkyl, halo, loweralkoxy, acyl, acyloxy, thio, acylthio, loweralkylthio, loweralkylsulfinyl, loweralkylsulfonyl; hydroxy, carboxy, and carbalkoxy;

$R_3$ and $R_8$ may also be cycloalkyl, cycloalkenyl, aryl and heteroloweralkylidenyl.

DETAILED DESCRIPTION OF THE INVENTION

The sunscreen preparations provided in accordance with the present invention contain as the essential active ingredient a compound of the formula:

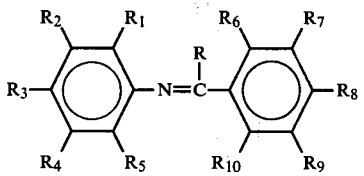

where:

R is hydrogen or alkyl;

$R_1$, $R_2$, $R_3$, $R_4$, $R_5$, $R_6$, $R_7$, $R_8$, $R_9$ and $R_{10}$ may be the same or different and are hydrogen, alkyl, cyano, nitro, amino, haloloweralkoxy, haloloweralkyl, halo, loweralkoxy, acyl, acyloxy, thio, acylthio, loweralkylthio, loweralkylsulfinyl, loweralkylsulfonyl; hydroxy, carboxy, and carbalkoxy;

$R_3$ and $R_8$ may also be cycloalkyl, cycloalkeny, aryl and heteroloweralkylidenyl.

The more preferred compounds for a method of topically treating inflammation embrace those compounds of the Formula II:

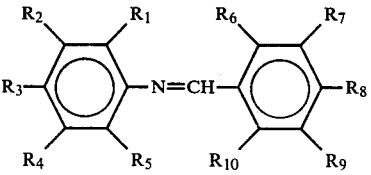

where:

$R_1$, $R_2$, $R_4$, $R_5$, $R_6$, $R_7$, $R_9$ and $R_{10}$ are hydrogen, alkyl, alkoxy, halo, haloloweralkyl, hydroxy, carboxy, carbalkoxy, and alkylsulfonyl. $R_3$ and $R_8$ are hydrogen, alkyl, alkoxy, carboxy, carbalkoxy, halo, cyano, alkylsulfonyl, alkylsulfinyl, haloloweralkyl, phenyl, and cyclohexyl.

In the descriptive portions of this invention, the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to about 7 carbon atoms which may be straight chained or branched;

"cycloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid by the removal of its hydroxyl group such as formyl, acetyl, propionyl, 3-carboxy-2-propenoyl, camphoryl, benzoyl, toluoyl or heteroyl such as pyridinoyl, piperidonyl, thenoyl, etc.

The compounds of this invention may be prepared by the following general procedures.

Condensation of an aniline derivative with benzaldehyde derivatives or phenyl ketones along the procedures as described by Gillman and Blatt, *Organic Synthesis*, Coll. Vol. I, 2nd Ed., N.Y., John Wiley and Sons, pages 80-81 will result in the desired product.

The following reaction equation illustrates this synthesis:

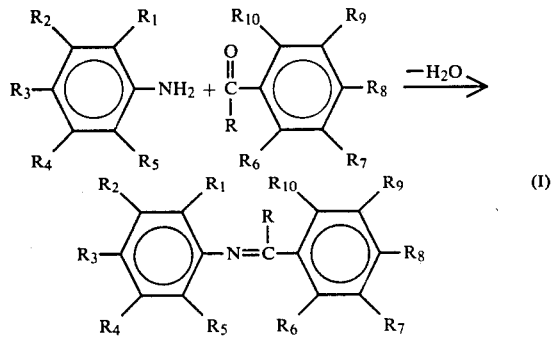

where R, $R_1$, $R_2$, $R_3$, $R_4$, $R_5$, $R_6$, $R_7$, $R_8$, $R_9$ and $R_{10}$ are as described above.

An alternate method for the production of certain compounds of Formula I involves the distillation of a product from a heated mixture of an aryl aldehyde or ketone and an aniline derivative at an elevated temperature and under a reduced pressure.

A still further method of preparing certain compounds of Formula I would be by condensation of a hindered aryl aldehyde or ketone and an aniline derivative by the azeotropic removal of water.

Appropriately desired end products having various substituents can be prepared at various stages of synthesis using suitable reactions in order to convert one group to another. Thus, for example, using conventional methods, a halogen group can be converted under Rosenmund Von Braun conditions to the nitrile compound. A nitro can be reduced to an amino which can be alkylated to the dialkylamino substituent. An hydroxy compound can be prepared by demethylation of a methoxy substituent. A Sandmeyer type reaction can be carried out on an amino compound to introduce a chloro, bromo, xanthate, hydroxyl or alkoxyl group. The xanthate can then lead to the mercapto by hydrolysis, this in turn can be alkylated to an alkylthio group which can be oxidized to alkylsulfinyl and alkylsulfonyl groups. A thiocyanato group may be removed by catalytic hydrogenation.

Among the suitable compounds which may be utilized in connection with the sunscreen and prostaglandin-inhibiting compositions of the present invention include:

N-benzylideneaniline
N-(hydroxybenzylidene)aniline
N-(carboxybenzylidene)aniline
N-(carbomethoxybenzylidene)toluidine
N-carboethoxybenylidene-m-toluidine
N-benzylidene-p-toluidine
N-(o-hydroxybenzylidene)-m-toluidine
N-(o-hydroxybenzylidene)-p-toluidine
N-(o-hydroxybenzylidene)-m-α,α,α-trifluorotoluidine
N-(o-hydroxybenzylidene)-o-α,α,α-trifluorotoluidine
N-(benzylidene-o-ethylaniline
N-benzylidene-o-hydroxyaniline
N-benzylidene-m-hydroxyaniline
N-benzylidene-p-hydroxyaniline
N-(o-hydroxybenzylidene)-o-hydroxyaniline
N-(m-hydroxybenzylidene)-o-hydroxyaniline
N-(p-hydroxybenzylidene)-o-hydroxyaniline
N-(o-hydroxybenzylidene)-m-hydroxyaniline
N-(m-hydroxybenzylidene)-m-hydroxyaniline
N-(p-hydroxybenzylidene)-m-hydroxyaniline
N-(o-hydroxybenzylidene)-p-hydroxyaniline
N-(m-hydroxybenzylidene)-p-hydroxyaniline
N-(p-hydroxybenzylidene)-p-hydroxyaniline
N-(2,3-dihydroxybenzylidene)-o-hydroxyaniline
N-(2,4-dihydroxybenzylidene)-o-hydroxyaniline
N-(2,5-dihydroxybenzylidene)-o-hydroxyaniline
N-(2,6-dihydroxybenzylidene)-o-hydroxyaniline
N-(3,4-dihydroxybenzylidene)-o-hydroxyaniline
N-(3,5-dihydroxybenzylidene)-o-hydroxyaniline
N-(2,3,4-trihydroxybenzylidene)-o-hydroxyaniline
N-(2,4,6-trihydroxybenzylidene)-m-hydroxyaniline
N-(3,4,5-trihydroxybenzylidene)-m-hydroxyaniline
N-(2,3-dihydroxybenzylidene)-p-hydroxyaniline
N-(2,4-dihydroxybenzylidene)-p-hydroxyaniline
N-(2,5-dihydroxybenzylidene)-p-hydroxyaniline
N-(2,6-dihydroxybenzylidene)-p-hydroxyaniline
N-(3,4-dihydroxybenzylidene)-p-hydroxyaniline
N-(3,5-dihydroxybenzylidene)-p-hydroxyaniline
N-(2,3,4-trihydroxybenzylidene)-p-hydroxyaniline
N-(2,4,6-trihydroxybenzylidene)-p-hydroxyaniline
N-(p-morpholinobenzylidene)aniline
N-(p-phenylbenzylidene)aniline
o-chlorobenzylideneaniline
m-chlorobenzylideneaniline
p-chlorobenzylideneaniline
N-benzylidene-o-chloroaniline
N-benzylidene-m-chloroaniline
N-benzylidene-p-chloroaniline
N-benzylidene-2,3-dichloroaniline
N-benzylidene-2,4-dichloroaniline
N-benzylidene-2,5-dichloroaniline
N-benzylidene-2,6-dichloroaniline
N-benzylidene-3,4-dichloroaniline
N-benzylidene-3,5-dichloroaniline
N-benzylidene-2,3,4-trichloroaniline
N-benzylidene-2,4,6-trichloroaniline
N-(o-chlorobenzylidene)-o-chloroaniline
N-(m-chlorobenzylidene)-o-chloroaniline
N-(p-chlorobenzylidene)-4-toluidine
N-(p-chlorobenzylidene)-o-chloroaniline
N-(o-chlorobenzylidene)-m-chloroaniline
N-(m-chlorobenzylidene)-m-chloroaniline
N-(p-chlorobenzylidene)-m-chloroaniline N-(o-chlorobenzylidene)-p-chloroaniline
N-(m-chlorobenzylidene)-p-chloroaniline
N-(p-chlorobenzylidene)-p-chloroaniline
N-(o-chlorobenzylidene)-o-fluoroaniline
N-(m-chlorobenzylidene)-o-fluoroaniline
N-(p-chlorobenzylidene)-o-fluoroaniline
N-(o-chlorobenzylidene)-m-fluoroaniline
N-(m-chlorobenzylidene)-m-fluoroaniline
N-(p-chlorobenzylidene)-m-fluoroaniline
N-(o-chlorobenzylidene)-p-fluoroaniline
N-(m-chlorobenzylidene)-p-fluoroaniline
N-(p-chlorobenzylidene)-p-fluoroaniline
N-(2,3-dichlorobenzylidene)-o-chloroaniline
N-(2,4-dichlorobenzylidene)-o-chloroaniline
N-(2,5-dichlorobenzylidene)-o-chloroaniline
N-(2,6-dichlorobenzylidene)-o-chloroaniline
N-(3,4-dichlorobenzylidene)-o-chloroaniline
N-(3,5-dichlorobenzylidene)-o-chloroaniline
N-(2,3,4-trichlorobenzylidene)-o-chloroaniline
N-(2,4,6-trichlorobenzylidene)-o-chloroaniline
N-(2,3-dichlorobenzylidene)-m-chloroaniline
N-(2,4-dichlorobenzylidene)-m-chloroaniline
N-(2,5-dichlorobenzylidene)-m-chloroaniline
N-(2,6-dichlorobenzylidene)-m-chloroaniline
N-(3,4-dichlorobenzylidene)-m-chloroaniline
N-(3,5-dichlorobenzylidene)-m-chloroaniline
N-(2,3,4-trichlorobenzylidene)-m-chloroaniline
N-(2,4,6-trichlorobenzylidene)-m-chloroaniline
N-(2,3-dichlorobenzylidene)-p-chloroaniline
N-(2,4-dichlorobenzylidene)-p-chloroaniline
N-(2,5-dichlorobenzylidene)-p-chloroaniline
N-(2,6-dichlorobenzylidene)-p-chloroaniline
N-(3,4-dichlorobenzylidene)-p-chloroaniline
N-(3,5-dichlorobenzylidene)-p-chloroaniline
N-(2,3,4-trichlorobenzylidene)-p-chloroaniline
N-(2,4,6-trichlorobenzylidene)-p-chloroaniline
o-fluorobenzylideneaniline
m-fluorobenzylideneaniline
p-fluorobenzylideneaniline
N-benzylidene-o-fluoroaniline
N-benzylidene-m-fluoroaniline
N-benzylidene-p-fluoroaniline
N-benzylidene-2,3-difluoroaniline
N-benzylidene-2,4-difluoroaniline
N-benzylidene-2,5-difluoroaniline
N-benzylidene-2,6-difluoroaniline
N-benzylidene-3,4-difluoroaniline
N-benzylidene-3,5-difluoroaniline
N-(o-chlorobenzylidene)-p-trifluoromethylaniline
N-benzylidene-2,3,4-trifluoroaniline
N-benzylidene-2,4,6-trifluoroaniline
N-(o-fluorobenzylidene)-o-fluoroaniline
N-(m-fluorobenzylidene)-o-fluoroaniline
N-(p-fluorobenzylidene)-o-fluoroaniline
N-(o-fluorobenzylidene)-m-fluoroaniline
N-(m-fluorobenzylidene)-m-fluoroaniline
N-(p-fluorobenzylidene)-m-fluoroaniline
N-(o-fluorobenzylidene)-m-fluoroaniline
N-(m-fluorobenzylidene)-m-fluoroaniline
N-(p-fluorobenzylidene)-m-fluoroaniline
N-(2,3-difluorobenzylidene)-o-fluoroaniline
N-(2,4-difluorobenzylidene)-o-fluoroaniline
N-(2,5-difluorobenzylidene)-o-fluoroaniline
N-(2,6-difluorobenzylidene)-o-fluoroaniline
N-(3,4-difluorobenzylidene)-o-fluoroaniline
N-(3,5-difluorobenzylidene)-o-fluoroaniline
N-(2,3,4-trifluorobenzylidene)-o-fluoroaniline
N-(2,4,6-trifluorobenzylidene)-o-fluoroaniline
N-(2,3-difluorobenzylidene)-m-fluoroaniline
N-(2,4-difluorobenzylidene)-m-fluoroaniline
N-(2,5-difluorobenzylidene)-m-fluoroaniline
N-(2,6-difluorobenzylidene)-m-fluoroaniline
N-(3,4-difluorobenzylidene)-m-fluoroaniline
N-(3,5-difluorobenzylidene)-m-fluoroaniline
N-(2,3,4-trifluorobenzylidene)-m-fluoroaniline
N-(2,4,6-trifluorobenzylidene)-m-fluoroaniline
N-(2,3-difluorobenzylidene)-p-fluoroaniline
N-(2,4-difluorobenzylidene)-p-fluoroaniline
N-(2,5-difluorobenzylidene)-p-fluoroaniline
N-(2,6-difluorobenzylidene)-p-fluoroaniline
N-(o-chlorobenzylidene)-p-bromoaniline
N-(2,4-dichlorobenzylidene)-p-bromoaniline
N-benzylidene-2-methyl-3-chloroaniline
N-benzylidene-2-methyl-4-chloroaniline
N-benzylidene-2-methyl-3-fluoroaniline
N-benzylidene-2-methyl-4-fluoroaniline
N-(o-chlorobenzylidene)-2-methyl-3-chloroaniline
N-(o-chlorobenzylidene)-2-methyl-4-chloroaniline
N-(o-chlorobenzylidene)-2-methyl-5-chloroaniline
N-(m-chlorobenzylidene)-2-methyl-3-chloroaniline
N-(m-chlorobenzylidene)-2-methyl-4-chloroaniline
N-(p-chlorobenzylidene)-2-methyl-3-chloroaniline
N-(p-chlorobenzylidene)-2-methyl-4-chloroaniline
N-(p-chlorobenzylidene)-2-methyl-5-chloroaniline
N-(m-fluorobenzylidene)-2,4-dichloroaniline
N-(o-fluorobenzylidene)-2,4-dichloroaniline
N-(p-fluorobenzylidene)-2,4-dichloroaniline
N-(o-fluorobenzylidene)-2-methyl-3-chloroaniline
N-(o-chlorobenzylidene)-2-methyl-3-chloroaniline
N-(o-hydroxybenzylidene)-2-methyl-3-chloroaniline
N-(o-methylbenzylidene)-2-methyl-3-chloroaniline
N-(o-ethylbenzylidene)-2-methyl-3-chloroaniline
N-(o-chlorobenzylidene)-2-trifluoromethyl-4-fluoroaniline
N-(o-chlorobenzylidene)-2-trifluoromethyl-4-fluoroaniline
N-(o-chlorobenzylidene)-2-trifluoromethyl-3-fluoroaniline
N-(p-chlorobenzylidene)-2-trifluoromethyl-3-fluoroaniline
N-(p-bromobenzylidene)-2-trifluoromethyl-3-fluoroaniline
N-(p-bromobenzylidene)-2-trifluoromethyl-4-fluoroaniline
N-(p-fluorobenzylidene)-2-trifluoromethyl-4-fluoroaniline
N-(p-phenylbenzylidene)-p-toluidine
N-(p-phenylbenzylidene)-p-bromoaniline
N-(p-phenylbenzylidene)-2-methyl-4-chloroaniline
N-(p-phenylbenzylidene)-2-methyl-4-fluoroaniline
N-(p-phenylbenzylidene)-2-chloro-4-bromoaniline
N-(3-chlor-4-cyclohexylbenzylidene)-4-fluoroaniline
N-(3-chloro-4-cyclohexylbenzylidene)-4-bromoaniline
N-(o-hydroxybenzylidene)-o-chloroaniline
N-(o-hydroxybenzylidene)-m-chloroaniline
N-(o-hydroxybenzylidene)-p-chloroaniline
N-(o-hydroxybenzylidene)-o-fluoroaniline
N-(o-hydroxybenzylidene)-m-fluoroaniline
N-(o-hydroxybenzylidene)-p-fluoroaniline
N-(o-hydroxybenzylidene)-2-methyl-3-chloroaniline
N-(o-hydroxybenzylidene)-2-methyl-4-chloroaniline
N-(o-hydroxybenzylidene)-2,3-dimethylaniline
N-(o-hydroxybenzylidene)-2,4-dimethylaniline
N-(o-hydroxybenzylidene)-o-toluidine
N-(o-hydroxybenzylidene)-m-toluidine
N-(o-hydroxybenzylidene)-p-toluidine N-(benzylidene)-2,4-dibromoaniline
N-(m-fluorobenzylidene)-2,4-dibromoaniline
N-(m-fluorobenzylidene)-2-methyl-4-iodoaniline
N-(o-fluorobenzylidene)-2,4-dibromoaniline
N-(o-fluorobenzylidene)-2-methyl-4-iodoaniline
N-(m-fluorobenzylidene)-2,4-dibromoaniline
N-(m-fluorobenzylidene)-2-methyl-4-iodoaniline
N-(m-fluorobenzylidene)-3-trifluoromethyl-4-chloroaniline
N-(o-fluorobenzylidene)-3-trifluoromethyl-4-chloroaniline
N-(p-fluorobenzylidene)-3-trifluoromethyl-4-chloroaniline
N-(acyloxybenzylidene)aniline
N-(carboxybenzylidene)-m-toluidine
N-(carbomethoxybenzylidene)-m-toluidine
N-(benzylidene-carboxyaniline
N-benzylidene-carbomethoxyaniline
N-benzylidene-methylthioaniline
N-benzylidene-methylsulfonylaniline
N-benzylidene-methylsulfinylaniline
N-benzylidene-acetylthioaniline
N-(carboxylbenzylidene)hydroxyaniline
N-(carboxylbenzylidene)chloroaniline
N-(carboxylbenzylidene)fluoroaniline
N-(methylsulfonylbenzylidene)hydroxyaniline
N-(methylsulfonylbenzylidene)chloroaniline
N-(acetyloxybenzylidene)hydroxyaniline
N-(carbomethoxybenzylidene)chloroaniline
N-(hydroxybenzylidene)carboxyaniline
N-(chlorobenzylidene)carboxyaniline
N-(dihydroxybenzylidene)carboxyaniline
N-(dichlorobenzylidene)carboxyaniline
N-(difluorobenzylidene)carboxyaniline
N-(dihydroxybenzylidene)methylsulfonylaniline
N-(dichlorobenzylidene)methylsulfonylaniline
N-(difluorobenzylidene)methylsulfonylaniline
N-(2,3,4-trihydroxybenzylidene)carboxyaniline
N-(3,5-dichlorobenzylidene)-p-carbomethoxyaniline
N-(4-carbomethoxybenzyliene)-dichloroaniline
N-(2,4,6-trichlorobenzylidene)carboxyaniline
N-(3,4,5-trifluorobenzylidene)carboxyaniline
N-(p-morpholinobenzylidene)carboxyaniline
N-(p-phenylbenzylidene)carboxyaniline
N-(methylsulfonylbenzylidene)chloroaniline
N-(carboxybenzylidene)chloroaniline
N-(p-carboxybenzylidene)-4-toluidine
N-(p-chlorobenzylidene)-2-[(5-methyl-4-imidozolyl)methyl mercapto]aniline
N-(2,3-dichlorobenzylidene)carboxyaniline
N-(2,4-dichlorobenzylidene)acetyloxyaniline
N-(2,5-dichlorobenzylidene)methylsulfonylaniline
N-(p-cyanobenzylidene)-3,5-dichloroaniline
N-(p-nitrobenzylidene)-3,5-dichloroaniline
N-(p-carbomethoxybenzylidene)-3,5-dichloroaniline
N-(p-methylsulfonylbenzylidene)-3,5-dichloroaniline
N-(p-chlorobenzyldiene)-2-carboethoxy-4-fluoroaniline
N-(p-carbomethoxybenzylidene)-4-methylaniline
N-(2,3,4-trichlorobenzylidene)-p-carboxyaniline
N-(2,4,6-trichlorobenzylidene)-p-carboxyaniline
N-(o-carboxybenzylidene)-p-trifluoromethylaniline
N-(halo-4-cyclohexylbenzylidene)-4-haloaniline
N-(3-chloro-4-cyclohexylbenzylidene)-4-fluoroaniline
N-(3-chloro-4-cyclohexylbenzylidene)-4-bromoaniline
N-(2,3-difluorobenzylidene)carboxyaniline
N-(2,4-difluorobenzylidene)carboxyaniline
N-(2,5-difluorobenzylidene)carboxyaniline
N-(2,6-difluorobenzylidene)carboxyaniline
N-(3,4-difluorobenzylidene)carboxyaniline
N-(3,5-difluorobenzylidene)carboxyaniline
N-(2,3,4-trifluorobenzylidene)carboxyaniline
N-(2,4,6-trifluorobenzylidene)methylsulfonylaniline
N-(2,3-difluorobenzylidene)methylsulfonylaniline
N-(2,4-difluorobenzylidene)acetyloxyaniline
N-(2,5-difluorobenzylidene)acetyloxyaniline
N-(2,6-difluorobenzylidene)acetyloxyaniline
N-(2,3,4-trifluorobenzylidene)carboxyaniline
N-(2,4,6-trifluorobenzylidene)carboxyaniline
N-benzylidene-2-methyl-3-carboxyaniline
N-benzylidene-2-methyl-4-carboxyaniline
N-benzylidene-2-methyl-3-acetyloxyaniline
N-benzylidene-2-methyl-4-acetyloxyaniline
N-(chlorobenzylidene)-2-methyl-3-carboxyaniline
N-(chlorobenzylidene)-2-methyl-4-carboxyaniline
N-(chlorobenzylidene)-2-methyl-5-carboxyaniline
N-(chlorobenzylidene)-2-methyl-3-chloroaniline
N-(chlorobenzylidene)-2-methyl-4-acetyloxyaniline
N-(p-carboxybenzylidene)-2-methyl-3-chloroaniline
N-(p-carboxybenzylidene)-2-methyl-4-chloroaniline
N-(p-carboxybenzylidene)-2-methyl-5-chloroaniline
N-(m-carboxybenzylidene)-2,4-dichloroaniline
N-(carboxybenzylidene)-2,4-dichloroaniline
N-(methylsulfonylbenzylidene)-2,4-dichloroaniline
N-(carboxybenzylidene)-2-methyl-3-chloroaniline
N-(methylsulfonylbenzylidene)-2-methyl-3-chloroaniline
N-(hydroxybenzylidene)-2-carboxy-3-chloroaniline
N-(methylbenzylidene)-2-carboxy-3-chloroaniline
N-(ethylbenzylidene)-2-methylsulfonyl-3-chloroaniline
N-(p-carboxybenzylidene)-2-trifluoromethyl-4-fluoroaniline
N-(p-carboxybenzylidene)-2-trifluoromethyl-3-fluoroaniline
N-(p-acetyloxybenzylidene)-2-trifluoromethyl-4-fluoroaniline
N-(p-phenylbenzylidene)-2-methyl-4-carboxyaniline
N-(p-phenylbenzylidene)-2-methyl-4-acetyloxyaniline
N-(p-phenylbenzylidene)-2-chloro-4-carboxyaniline
N-(3-chloro-4-cyclohexylbenzylidene)-4-carboxyaniline
N-(o-carboxybenzylidene)-2,3-dimethylaniline
N-(o-carboxybenzylidene)-2,4-dimethylaniline
N-(o-methylsulfonylbenzylidene)-o-toluidine
N-(o-acetyloxybenzylidene)-m-toluidine
N-(o-methylsulfinylbenzylidene)-p-toluidine
N-(fluorobenzylidene)-3-trifluoromethyl-4-carboxyaniline
N-(fluorobenzylidene)-3-trifluoromethyl-4-acetyloxyaniline
N-(fluorobenzylidene)-3-trifluoromethyl-4-methylsulfonylaniline These active materials are applied to the skin in combination with a compatible carrier material which may be aqueous, alcoholic, fatty or a combination of these. Carrier materials as contemplated herein include those materials generally utilized as a base for sunscreen preparations such as, for example, creams, milks, ointments, gels, oils, lotions, aerosol sprays or the like. Such carrier materials, in order to be suitable, must be selected on a basis of their dermatological acceptability and compatibility with the specific active ingredient of the present invention which is utilized. Preferred among carrier formulations for the sunscreen agents of the present invention are creams, milk, ointments, lotions and aerosols.

Examples of suitable carrier materials for the formulation of the sunscreen compositions of the invention include the paraffins, waxes, vegetable or animal oils and fats such as, for example, olive oil, sesame oil, peanut oil and the like, wool fat, spermaceti, esters of fatty acids such as stearic, palmitic and oleic as well as the acids themselves, glycerides of said acids, ethyl, isopropyl, cetyl, stearyl and palmityl alcohols, emulsifying agents of all common types, e.g., nonionic, anionic or cationic suitable for the preparation of both water-in-oil and oil-in-water emulsions, thickeners such as, for example, the commercially available cellulose ethers, trajacanth, alginic acid or salts thereof and the like. A particularly preferred emulsifying agent is polyoxyethylene stearyl ether having a molecular weight of about 700 and commercially available under the trademark Brij J by Atlas Powder Co., Wilmington, Delaware. Additional additives which may be incorporated into the sunscreen preparations of the invention are preservatives, buffers, pH regulators to adjust the pH thereof to slightly acidic, perfumes, physiologically compatible dyestuffs and the like. Other agents which have medicinal or therapeutic value may also be incorporated in the compositions of the invention. Where the preparations of the invention are in the form of aerosol sprays or foams, suitable conventional propellants, i.e. polyhalogenated hydrocarbons are also included therein. It is contemplated that where the compositions of the invention are in aerosol form, the propellant will comprise about 10% by weight of said compositions.

The concentration of the active sunscreen ingredient in dermatologically acceptable carrier preparations such as contemplated herein is between about 1% and about 30% by weight and preferably between about 2% and about 5% by weight.

Wherein the sunscreen preparations of the invention contain mixtures of more than one of the active ingredients, such active ingredients may be combined in any proportions. It is preferred, however, to combine two or more of such ingredients in approximately equimolar concentrations.

Compositions in accordance with this invention afford excellent protection from the erythemal rays of the sun. Additionally, they are effective in preventing and treating painful sunburn. These compositions may be applied freely to the skin. As with any conventional skin treatment preparation, such amounts vary with the exposure conditions, the sensitivity and the pigmentation of the skin of the user, and the like. Therefore, the effective amount of the preparations of the invention may be chosen within the discretion of the user.

The following examples serve further to illustrate the invention, but are not intended to define or to limit the scope of the invention, which is defined in the appended claims.

EXAMPLE 1

A sunscreen lotion in milk form, having the following composition:

| | |
|---|---|
| Hydrogenated, ethoxylated (10 mol) lanolin | 2.0 g. |
| Triglyceride of fatty acid of coconut oil | 7.0 g. |
| Cetylalcohol | 0.6 g. |
| Stearylalcohol | 0.6 g. |
| Paraffin oil (light weight) | 5.0 g. |
| N-(o-chlorobenzylidene)-3-chloro-2-methylaniline | 2.5 g. |
| Stearic acid | 3.0 g. |
| Demineralized water | 74.0 g. |
| Triethanolamine | 0.8 g. |
| Perfume | 0.5 g. |
| Carboxyvinylpolymer | 2.0 g. |
| Conservation agent | 2.0 g. | was manufactured as follows:

A mixture of 2.0 g. hydrogenated, ethoxylated (10 mol) lanolin, 7.0 g. triglyceride of fatty acid of coconut oil, 0.6 g. cetylalcohol, 0.6 g. stearyl alcohol, 5.0 g. paraffin oil, 2.5 g. N-(o-chlorobenzylidene)-3-chloro-2-methylaniline and 3.0 g. of stearic acid was melted at 70° C. After addition of 2.0 g. carboxyvinylpolymer in 74.0 g. demineralized water were added at 70° C. with stirring to the resulting suspension. The mixture was stirred for 15 minutes and then cooled. 0.8 g. of triethanolamine and 0.5 g. of perfume were added at 60° C. and 45° C., respectively. The resulting mixture was stirred until cold and a white milk, which was stable at 3,000 rpm for 1 hour, was obtained.

Other lotions identical to that described immediately above are prepared by replacing the N-(o-chlorobenzylidene-3-chloro-2-methylaniline with any of the active compounds previously mentioned.

EXAMPLE 2

A sunscreen product, composed of:

| | |
|---|---|
| Triglyceride of fatty acid of coconut oil | 56.3 g. |
| Cetylalcohol | 2.6 g. |
| Stearylalcohol | 10.6 g. |
| Paraffin oil (light weight) | 8.0 g. |
| N-benzylidene-p-toluidine | 5.0 g. |
| Demineralized water | 12.2 g. |
| Triethanolamine | 0.8 g. |
| Perfume | 0.5 g. |
| Carboxyvinylpolymer | 2.0 g. |
| Conservation agent | 2.0 g. | was manufactured as follows:

A mixture of 56.3 g. triglyceride of fatty acid of coconut oil, 2.6 g. cetylalcohol, 10.6 g. stearyl alcohol, 5.0 g. paraffin oil and 5.0 g. N-benzylidene-p-toluidine was mixed at 70° C. 12.0 g. carboxyvinylpolymer in 12.2 g. demineralized water were added at 70° C. with stirring to the resulting suspension. The mixture was stirred for 15 minutes and then cooled. 0.8 g. of triethanolamine and 0.5 g. of perfume were added at 60° C. and 45° C., respectively. The resulting mixture was stirred until cold and a lotion, which was stable at 3,000 rpm for 1 hour, was obtained.

Other preparations identical to that described immediately above are prepared by replacing the N-benzylidene-p-toluidine with any one of the aforementioned active compounds.

EXAMPLE 3

An ointment was prepared by first mixing 5.0 g. of p-carboxybenzylidene-2-chloroaniline in a hot mixture of 57.5 g. of distilled water. 11.5 g. of propylene glycol and 1 ml. of concentrated ammonia solution. The resulting mixture was heated to 75° C. and added with stirring to a hot (75° C.) mixture of 17.0 g. of glycerine, 4.0 g. of a polyoxyethylene stearyl ether having a molecular weight of about 700. Lactic acid was added while the emulsion was still hot in order to adjust to a pH approximating that of the skin, i.e. about 5.5. After cooling, the resulting cream was further worked utilizing a three-roller frame and filled into tubes.

The product had excellent properties in protecting the human skin against ultraviolet and visible light rays when spread out over selected areas of the body.

EXAMPLE 4

An ointment was prepared by first mixing 7.0 g. N-(4-carbomethoxybenzylidene)-3,5-dichloroaniline in a hot mixture of 53.93 g. of distilled water, 14 g. of propylene glycol and 1 ml. of concentrated ammonia solution. The resulting mixture was heated to 75° C. and added with stirring to a hot (75° C.) mixture of 17.0 g. of isopropyl myristate, 4.0 g. of glycerine and 4.0 g. of a polyoxyethylene stearyl ether, molecular weight about 700. Lactic acid was then added to the hot emulsion to adjust the pH thereof to approximate the pH of the skin, i.e. about 5.5. After cooling, the resulting cream was further worked using a three-roller frame and filled into tubes.

EXAMPLE 5

An ointment was formed by first mixing 4.0 g. N-(4-nitrobenzylidene)-3,5-dichloroaniline in a hot mixture of 60.3 g. of distilled water, 11.5 g. of propylene glycol and 10.1 g. of sodium hydroxide. The resulting solution was heated to 75° C. and added with stirring to a hot (75° C.) mixture of 15.0 g. isopropyl palmitate, 5.0 g. of glyceryl trioleate and 3.0 g. of polyoxyethylene stearyl ether. Lactic acid was added to the hot emulsion to adjust the pH thereof to about 5.5. After cooling, the resulting cream was further worked using a three-roller frame and filled into tubes. It had excellent sunscreen properties when applied to the human skin.

EXAMPLE 6

An ointment was formed as above by first mixing 7.0 g. N-(4-methylsulfonylbenzylidene)-3,5-dichloroaniline in a hot mixture of 60.83 g. of distilled water, 11.5 g. of propylene glycol and 0.1 g. of sodium hydroxide. The resulting solution was heated to 75° C. and added with stirring to a hot (75° C.) mixture of 13.0 g. polyol diester of capric acid, 5.0 g. of isopropyl myristate and 5.0 g. of polyoxyethylene stearyl ether. Lactic acid was added to the hot emulsion to adjust the pH thereof to about 5.5. After cooling, the resulting cream was further worked using a three-roller frame and filled into tubes. The product had excellent properties when used as a sunscreen.

EXAMPLE 7

A prostaglandin-inhibiting composition having the following composition:

| | | |
|---|---|---|
| Hydrogenated, ethoxylate (10 mol.) lanolin | 1.8 g. | |
| Triglyceride of fatty acid of coconut | 7.0 g. | |
| Cetylalcohol | 0.6 g. | |
| Stearylalcohol | 0.6 g. | |
| Paraffin oil (lightweight) | 5.0 g. | |
| N-(p-carboxylbenzylidene)-3-chloro-2-methylaniline | 0.75 g. | |
| Stearic acid | 3.0 g. | |
| Demineralized water | 72.2 g. | |
| Triethanolamine | 0.8 g. | |
| Perfume | 0.5 g. | |
| Carboxyvinylpolymer | 2.0 g. | |
| Conservation agent | 2.0 g. | | was manufactured as follows:

A mixture of 1.8 g. hydrogenated, ethoxylated (10 mol.) lanolin, 7.0 g. triglyceride of fatty acid of coconut, 0.6 g. cetylalcohol, 0.6 g. stearyl alcohol, 5.0 g. paraffin oil, 0.05 g. hydrocortisone and 3.0 g. of stearic acid was blended at 70° C. After addition of 0.75 g. N-(p-carboxylbenzylidene)-3-chloro-2-methylaniline, 2.0 g. carboxyvinylpolymer in 72.2 g. demineralized water were added at 70° C. with stirring to the resulting suspension. The mixture was stirred for 15 minutes and then cooled. 0.8 g. of triethanolamine and 0.5 g. of perfume were added at 60° C. and 45° C., respectively. The resulting mixture was stirred until cold and a white milk, which was stable at 3,000 rpm for one hour was obtained. Viscosity: 6000 Cp (Brockfield, Spindel, 5, 10 rpm).

EXAMPLE 8

A prostaglandin-inhibiting composition was prepared as follows:

0.5 g. of N-4-chlorobenzylidene)-4-chloro-2-methylaniline and 0.20 g. N-(4-hydroxybenzylidene)-2-methyl-3-chloroaniline are predispersed in 30.0 g. of propylene glycol. The mixture is then homogenized into 97.4 g. of finished cream, ointment or lotion following a modification of any one of the procedures described in F. W. Martin et al, "Remington's Pharmaceutical Sciences", 14th Ed., Mack Publishing Co., Easton, Pennsylvania (1965).

We claim:

1. A method of protecting human skin from erythema caused by ultraviolet and visible light radiation and for inhibiting the formation of prostaglandins in humans resulting from the radiation which comprise applying to the skin an effective amount of a compound of the formula:

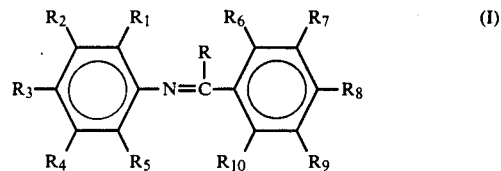

where:
R is hydrogen or alkyl;
$R_1$, $R_2$, $R_3$, $R_4$, $R_5$, $R_6$, $R_7$, $R_8$, $R_9$, and $R_{10}$ may be the same or different and are
hydrogen,
alkyl,
nitro,
amino,
haloloweralkoxy,
haloloweralkyl,
halo,
loweralkoxy,
hydroxy,
carboxy and
carbalkoxy; and
$R_3$ and $R_8$ may also be cycloalkyl, cycloalkenyl and aryl.

2. The method of claim 1 where applied is N-(o-chlorobenzylidene)-3-chloro-2-methylaniline.

3. The method of claim 1 where the compound applied is N-(2-methyl-3-chlorobenzylidene)-2-hydroxyaniline.

4. The method of claim 1 where the compound applied is o-hydroxybenzylideneaniline.

5. The method of claim 1 where the compound applied is N-(p-nitrobenzylidene)-3,5-dichloroaniline.

6. The method of claim 1 where the compound applied is N-(4-chlorbenzylidene)-3,5-dichloroaniline.

7. The method of claim 1 where the compound applied is N-(p-chlorobenzylidene)-2-methyl-3-chloroaniline.

8. The method of claim 1 where the compound applied is N-(p-carbomethoxybenzylidene)-3,5-dichloroaniline.

9. The method of claim 1 where the compound applied is N-(m-chlorobenzylidene)-4-fluoroaniline.

10. The method of claim 1 where the compound applied is N-(benzylidene)-3,5-dichloroaniline.

11. The method of claim 1 where the compound applied is N-(p-chlorobenzylidene)-2-carboethoxy-4-fluoroaniline.

12. The method of claim 1 where the compound applied is N-(p-phenylbenzylidene)-4-bromoaniline.

13. The method of claim 1 where the compound applied is N-(o-chlorobenzylidene)-4-fluoroaniline.

14. The method of claim 1 where the compound applied is N-(benzylidene)-2-methyl-4-fluoroaniline.

15. The method of claim 1 where the compound applied is N-(p-chlorobenzylidene)-m-fluoroaniline.

16. The method of claim 1 where the compound applied is N-(p-chlorobenzylidene)-m-chloroaniline.

17. The method of claim 1 where the compound applied is N-(o-chlorobenzylidene)-2-methyl-4-chloroaniline.

18. The method of claim 1 where the compound applied is N-(p-phenylbenzylidene)-2-chloro-4-bromoaniline.

19. The method of claim 1 where the compound applied is N-(p-chlorobenzylidene)-2-methyl-3-chloroaniline.

20. The method of claim 1 where the compound applied is N-(p-chlorobenzylidene)-2-methyl-4-chloroaniline.

21. The method of claim 1 where the compound applied is N-(3-chloro-4-cyclohexylbenzylidene)-4-fluoroaniline.

22. The method of claim 1 where the compound applied is N-(3-chloro-4-cyclohexylbenzylidene)-4-bromoaniline.

23. The method of claim 1 where the compound applied is N-(p-phenyl)benzylidene-p-methylaniline.

24. The method of claim 1 where the compound applied is N-(p-carbomethoxybenzilidene)-4-methylaniline.

25. The method of claim 1 where the compound applied is N-(p-phenylbenzylidene)aniline.

26. The method of claim 1 where the compound applied is N-(2,6-dichlorobenzylidene)-p-chloroaniline.

27. The method of claim 1 where the compound applied is N-benzylidene-o-toluidine.

28. The method of claim 1 where the compound applied is N-(4-chlorobenzylidene)-4-fluoro-2-trifluoromethylaniline.

29. The method of claim 1 where the compound applied is N-(p-bromobenzylidene)-4-fluoro-2-trifluoromethylaniline.

30. The method of claim 1 where the compound applied is N-(p-fluorobenzylidene)-2-trifluoromethylaniline.

31. The method of claim 1 where the compound applied is N-(o-chlorobenzylidene)-3-chloroaniline.

* * * * *